United States Patent [19]

Beuzard et al.

[11] Patent Number: 5,125,264
[45] Date of Patent: Jun. 30, 1992

[54] DEVICE AND APPARATUS FOR DETECTING AND MEASURING BY ECHOGRAPHY PARTICLES SETTLING IN A FLUID

[75] Inventors: Yves Beuzard, Paris; Michel Boynard, Saint Maur; Roger Guillet, Les Clayes sous Bois; Mahmoud Razavian, Thiais, all of France

[73] Assignee: Universite Rene Descartes, France

[21] Appl. No.: 664,507

[22] Filed: Mar. 5, 1991

Related U.S. Application Data

[63] Continuation of Ser. No. 579,210, Sep. 7, 1990, abandoned, which is a continuation of Ser. No. 372,658, Jun. 20, 1989, abandoned.

[30] Foreign Application Priority Data

Jun. 21, 1988 [FR] France ............................ 88 08229

[51] Int. Cl.[5] ............................................. G01N 31/02
[52] U.S. Cl. .................................................... 73/61.75
[58] Field of Search ............... 73/61.4, 865.5, 597, 73/598, 609, 629

[56] References Cited

U.S. PATENT DOCUMENTS 4,014,650 3/1977 Sigelmann.
4,801,428 1/1989 Homolko et al. .................... 73/61.4

FOREIGN PATENT DOCUMENTS 1073631 2/1984 U.S.S.R. ............................. 76/61.4

OTHER PUBLICATIONS

"Ultrasonic Interferometry Application to Study of Blood", M. Boyard et al., Annual International Conference of the IEEE Engineering in Medicine and Biology Society, vol. 12, No. 1, 1990.
"Effect of Flow Disturbance on Ultrasonic Backscatter From Blood", K. K. Shung et al., Journal of the Acoustical Society of America, vol. 75, No. 4, Apr. 1984, pp. 1265–1272.
"Attenuation and Speed of 10 MHz Ultrasound in Canine Blood of Various Packed-Cell Values at 37° C.", D. J. Hughes et al., Medical & Biological Engineering & Computing, vol. 17, No. 5, Sep. 1979, pp. 619–622.
"Evaluation of Red Blood Cell Aggregate Size by Ultrasonic Backscattering", M. Boynard et al., Proceedings of the IEEE Ninth Annual Conference of the Engineering in Medicine and Biology Society, Nov. 13–16, 1987, pp. 688–689, IEEE.
"Aggregation of Red Blood Cells Studies by Ultrasound Backscattering", M. Boynard et al., Biorheology, vol. 24, 1987, pp. 451–461, Pergamon Journal Ltd., U.S.

Primary Examiner—Robert Raevis
Attorney, Agent, or Firm—Armstrong, Nikaido, Marmelstein, Kubovcik & Murray

[57] ABSTRACT

The device chiefly includes a thermostatically controlled measuring cell (1) with which is associated a transmitting-receiving ultrasonic probe (2). The cell consists of a cavity (10) divided half way up by a thin plate (11). The upper chamber above the plate is designed to receive a suspension (13) of particles while the probe is located in the lower chamber below the plate. The upper face (14) of the probe is separated from the plate.

8 Claims, 6 Drawing Sheets

DEVICE AND APPARATUS FOR DETECTING AND MEASURING BY ECHOGRAPHY PARTICLES SETTLING IN A FLUID

FIELD OF THE INVENTION

The present invention, which relates to a device and an apparatus for analyzing by ultrasonography, particles settling in a fluid. The present invention consists more precisely of a device whose operation is based on the interference of two ultrasonic waves which makes it possible to determine the size of the particles, their rate of sedimentation and their compaction once sedimentation is completed.

BACKGROUND OF THE INVENTION

This device has been used to study organic particles (polystyrene, etc.) and biological particles (red blood cells) and, particularly in the case of the latter, their state of aggregation. The device and the apparatus described above make it possible to study, under advantageous conditions, the properties of particles (size, density, compaction, aggregation) as well as the state of the sediment formed. The rheological properties of the blood are largely governed by those of the red blood cells, on account of their large concentration, and they depend upon the deformability and aggregatability of these particles. Consequently, it is important in hospital practice to determine accurately the state of aggregation, or the agglutination of these cells. To evaluate the aggregation of the red blood cells with one another, usually the rate of sedimentation of the blood in the plasma is measured. The rate of sedimentation depends on the density of the red blood cells and the plasma, depends on the viscosity of the plasma and depends on the size of the red blood as well as of the aggregates. One classical method consists in measuring the height of a column of plasma above the plasma-blood interface after the first and second hour of sedimentation. It is also possible, on the basis of a curve of sedimentation obtained as a function of time, to determine the maximum rate of sedimentation of the red blood cells by measuring the greatest slope of the tangent to the sedimentation curve.

Ultrasonic methods can also be used. These are based on interactions, particularly the diffusion of the ultrasonic waves, with the substance concerned. It is known, indeed, that the intensity of an ultrasonic beam that propagates through a medium decreases as a function of the distance travelled. This attenuation of intensity of the ultrasonic beam is derived from a) the reflection occurring on the surface of elements constituting the medium and whose size is greater than the wavelength of the ultrasonic wave, from b) the diffusion of the beam which occurs when the size of the particles in suspension in the medium is less than or equal to the wavelength of the ultrasonic wave used, or from c) the absorption of ultrasounds which depends on the thickness and on the nature of the medium the ultrasonic wave travelled through. The interaction between the ultrasonic waves and the blood at the frequencies habitually used in medical diagnosis always gives rise to diffused waves. Analysis of the amplitude and frequency of the diffused waves yields information on the size, the nature and the movement of this obstacle. Experiments analyzing the amplitude of ultrasonic waves have been conducted in this connection and it has been possible to measure the variations in the back scattering coefficient of ultrasonic waves for blood suspensions as a function of the sedimentation rate of the red blood cells and it has been possible to identify a difference between non-aggregated and aggregated red blood cells.

SUMMARY OF THE INVENTION

The object of the present invention is to provide a device and an apparatus for detecting and analyzing, by echography, particles settling in a fluid using a source of ultrasonic waves emitted towards the suspension and a means for detecting and analyzing the waves reflected by the solid/sediment and sediment/suspension interfaces. The device essentially comprises a thermostatically controlled measuring cell which is associated with a transmitting-receiving ultrasonic probe. An A mode echograph ensures the generation of electric pulses with a variable repetition period that excite the probe, and also ensures detection and conversion of the ultrasonic signal reflected by each interface into an electric signal. A system for acquiring the signal introduces a programmable delay in relation to the transmission from the probe. A device for sampling the signal stroboscopically in a given time slot is provided. A device is also provided for digitally reconstituting the echo from the time slot and for supplying a screen with the representative curves.

More precisely, the measuring cell comprises two cavities separated by a thin plate, which is fixed or removable. One of the cavities is designed to receive the suspension of particles while the transmitting-receiving ultrasonic probe is located in the second cavity. The measuring cell is integrated in a thermostatically controlled enclosure.

The probe is positioned in such a way that the ultrasonic field is perpendicular to the plate and it is maintained by a tight plug which is provided with a small closable conduit. The cavity of the probe contains some fluid between the plate and the probe. The probe is made of a material that can emit ultrasounds and its operating frequency is dependent on the particles to be studied.

According to other features of the invention, the echograph detection module is constituted by an amplifier formed by an integrated circuit, a rectifier that operates on the principle of full-wave rectification with pre-biased diodes and an analog filter. It is also possible to carry out frequency analysis of the non-rectified signal.

A module for acquiring the signal makes it possible to introduce a programmable delay in relation to transmission by the probe and includes a sample and hold device and an analog/digital converter. A time window enables the electronic signal to be sampled in a time slot that is also programmable. The time window can thus be positioned on the echo generated by the interface between the plate and the suspension before an electronic circuit samples the electric signal contained in the window with the help of a delay with an adjustable time step P. It will be noted that a means is provided for stroboscopically sampling the reflected signal.

Further features and advantages of the invention will emerge as a result of reading the following description of one form of the embodiment which is to be considered by way of an example and which refers to the annexed drawings.

DESCRIPTION OF THE PREFERRED EMBODIMENTS

Figure 1:
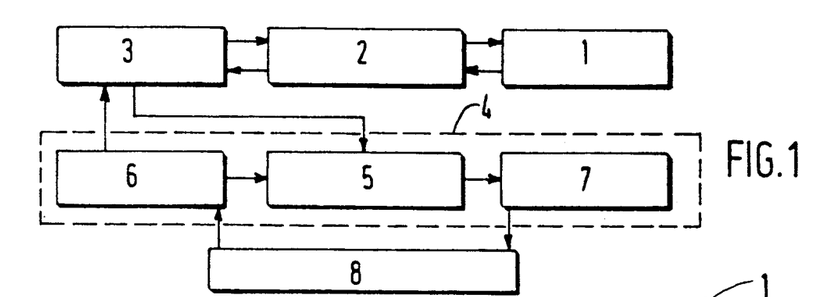
FIG. 1 is a block diagram of the device according to the invention.

The block diagram in FIG. 1 illustrates the device that embodies a thermostatically controlled measuring cell 1, a transmitting-receiving ultrasonic probe 2, an A mode echograph 3, a signal acquisition module 4 including a sample and hold device 5 functioning with a programmable delay 6 in relation to transmission, and an analog/digital converter 7. A micro-computer 8 effects the calculations and enables the results to be presented.

Figures 2, 3:
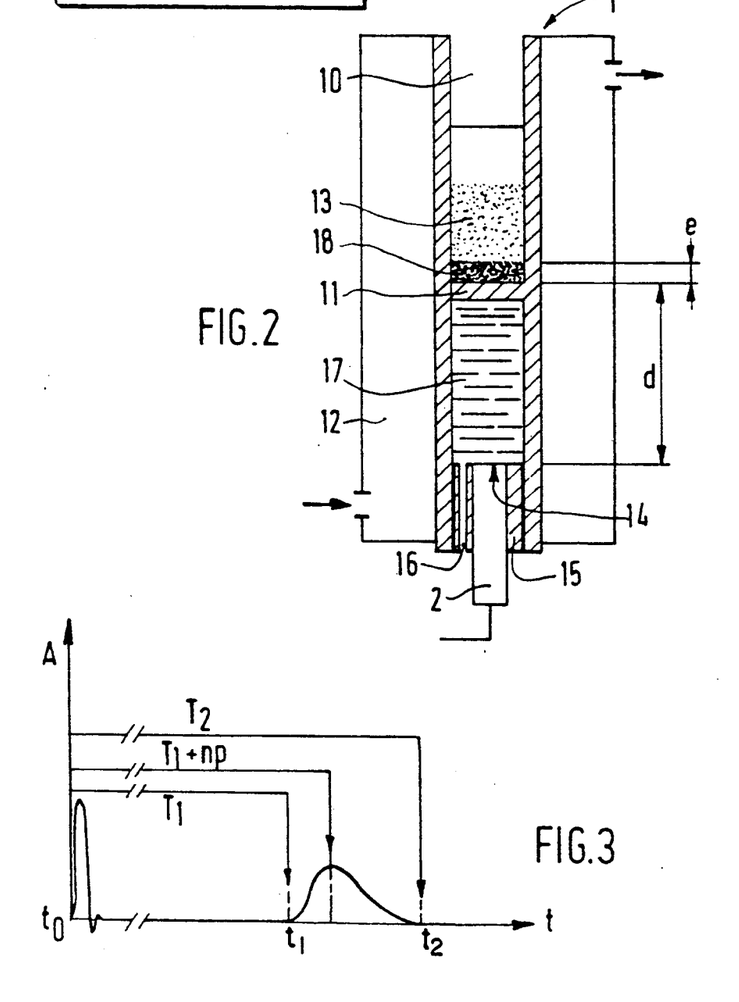
FIG. 2 is a schematic view of the measuring cell.
FIG. 3 is a curve illustrating stroboscopic acquisition in a given time slot.

The measuring cell 1 shown in FIG. 2 takes the form of a vertical bar hollowed out over its entire height to form a cylindrical cavity 10 integrated in a thermostatically controlled enclosure 12 maintaining its temperature at the desired level. The cavity is split into two by a thin plate 11 positioned perpendicular to the axis of the cylinder. The upper chamber above the plate 11 is designed to receive a suspension 13 of particles. At the base of the lower chamber below the plate is mounted the ultrasonic probe 2 which will be discussed later. The upper face 14 of the probe is separated from the upper face of the plate by a distance d equal to the limit of the near and remote ultrasonic fields. Probe 2 is positioned in the cavity by a tight plug 15 which closes the cavity. This plug has a small closable conduit 16 by means of which a volume of fluid 17 can fill the cavity between the plate and the probe, and plays the part of an acoustic seal. It is possible to invert the positions of the cavities for receiving respectively the suspension and the probe.

Before specifying the nature and the function of the elements illustrated in FIG. 1, there is given below a brief description of the mode of operation of an apparatus embodying the measuring cell already described.

An electric pulse generator, operating at a given repetition frequency, excites a material capable of emitting ultrasounds by means of the probe 2. Each time the material is excited by the generator, the probe emits an ultrasonic burst of a given duration, corresponding for example to a few periods, which is propagated through the fluid 17, towards plate 11 and suspension 13. As the burst travels, it loses one part of its energy through absorption and another part through reflection at the two faces of the plate 11. The ultrasonic wave part reflected by the two faces of the plate is collected by probe 2. The probe 2 is also a receiver, which converts the reflected wave part into an electric signal that depends on the time taken by the ultrasonic wave to travel to and fro between the probe and the plate. This signal must, quite clearly, be displayed on the screen of an oscilloscope. We shall see later how the introduction of a programmable delay, in relation to the excitation of the probe, makes it possible to measure the amplitude of the echos detected. It is possible, moreover, to carry out frequency analysis.

Of the elements defined in connection with FIG. 2, probe 2 constitutes an essential component of measuring cell 1. This ultrasonic probe 2 is formed of a material capable of emitting ultrasounds with a center frequency that can vary from 1 to 50 MHz (for example 8 MHz) and which operates in transmitting and receiving modes. The operating frequency is chosen as a function of the measurement contemplated.

The echograph 3 in FIG. 1 is composed of a) a generator of electric pulses, with a variable repetition period, which excites probe 2, b) a detection module rectifying and filtering the electric signal from the probe, and c) an oscilloscope enabling the echos to be visually displayed. The generation of the electric pulses is made by a capacitive discharge electric pulse generator whose pulse repetition frequency is adjustable. Using an electric damper or by modifying its load capacity value, it is possible to vary the amplitude and the duration of the pulse. The detection module of echograph 3 is constituted by an amplifier formed by 1) an integrated circuit, 2) a rectifier functioning on the principle of full-wave rectification with pre-biased diodes and an analog filter. The detection module rectifies and filters the electric signal from the probe.

Signal acquisition module 4 in FIG. 1 includes a sample and hold device 5 operating with programmable delay 6 in relation to transmission and an analog/digital converter 7. A time window enables the electric signal to be sampled in a time slot (t1, t2), which is also programmable. It is thus possible to analyze the sound signal from a slice having a thickness such as that of a sedimented layer 18 obtained above plate 11. Times t1 and t2 are determined in such a way that the time window includes the echo from the plate-sedimented layer interface.

Sample and hold device 5 is activated with a variable delay. It samples, following each pulse, the value of the amplitude of the electric signal from the plate-sedimented layer interface, located at the distance 2d. The rectified electric signal represents the reflected wave from the interface between plate 11 and suspension 13. The analog/digital converter 7 is used to digitize the amplitude of the sampled signal, which is then stored in the memory of micro-computer 8. The micro-computer 8 makes it possible to reconstitute digitally the analog signal.

Once the time window is positioned on the echo generated by the interface between plate 11 and suspension 13, an electronic circuit samples the electric signal contained in the window, with the help of an adjustable delay with a step p. FIG. 3 illustrates the principle of stroboscopic acquisition of the signals reflected in a time slot from t1 to t2. The X axis shows the time t and the Y axis the amplitude A of the signal. At time t0, a peak represents the transmission of an ultrasonic wave. The first acquisition illustrated by the occurrence of the start of a reflected signal takes place at time t1. The following acquisition is effected at time t1+p after the following transmission, and so on. Generally speaking, the nth. acquisition is effected at the time tn after the nth. transmission with tn=t1+np and t1<tn<t2. The reflected signal is sampled with the help of a certain number of acquisitions. Once sampled, the amplitude of the signal is digitized using the converter and is stored in the memory of the micro-computer. All of the sampled points belonging to the window are thus stored and then enable the analog signal to be reconstituted digitally. Once the time window is positioned on the echo generated by the interface between plate 11 and suspension 13, an electronic circuit samples the electric signal contained in the window, with the help of an adjustable delay with a step p.

One of the registers of the micro-computer is used as a master clock and triggers the pulse generator, which itself supplies three pulses at each cycle: a delay pulse to vary the position of the sampler, a sampling pulse to sample the amplitude of the echo, then a conversion pulse to operate the converter.

A means has been provided to synchronize the operation of the echograph, to select the position and the duration of the sampling window and the storage and editing of the results.

With measuring cell 1 and the device described above, it is possible to follow the variations in the amplitude of the echos from the plate 11-sedimented layer 18 and sedimented layer 18-suspension 13 interfaces due to the acoustic impedance of a sedimented layer is different from that of the plate and different from that of the suspension and each discontinuity in acoustic impedance gives rise to an echo.

When the two interfaces, plate 11-sedimented layer 18 and sedimented layer 18-suspension 13, are sufficiently close to one another, the ultrasonic waves reflected therefrom interfere with each other and the amplitude of the resultant wave makes it possible to identify layers of sedimented particles with a thickness far less than the wavelength of the ultrasonic. Consequently, it is possible to study, as a function of time, the sedimentation of such particles on the plate due to the amplitude of the resultant wave.

We can deduce therefrom, for example, the rate at which the particles accumulate on the plate and thus settle in a suspension and obtain information therefrom on the properties of the sediment and, possibly, on the state of aggregation of the particles. The device and the apparatus according to the invention can find interesting applications in the study of normal blood and pathological blood, but the invention is not limited to this preferred field of use. It also covers all those applications in which information is sought on the properties of solid particles in a suspension (size, density, compaction, aggregation).

EXAMPLES OF RESULTS

I—Suspensions of Particles

A suspension of particles of copolymer-styrene-divinyl-benzene (Mitsubishi Chemical Industries) was prepared by suspending these particles in a PBS buffer solution (10 mM of Na phosphate; 0.15M of NaCl; pH=7.4; osmolality=300 mosm/kg; density=1.005) at a volume concentration of 1%.

A. Example of curve obtained.

Figure 4:
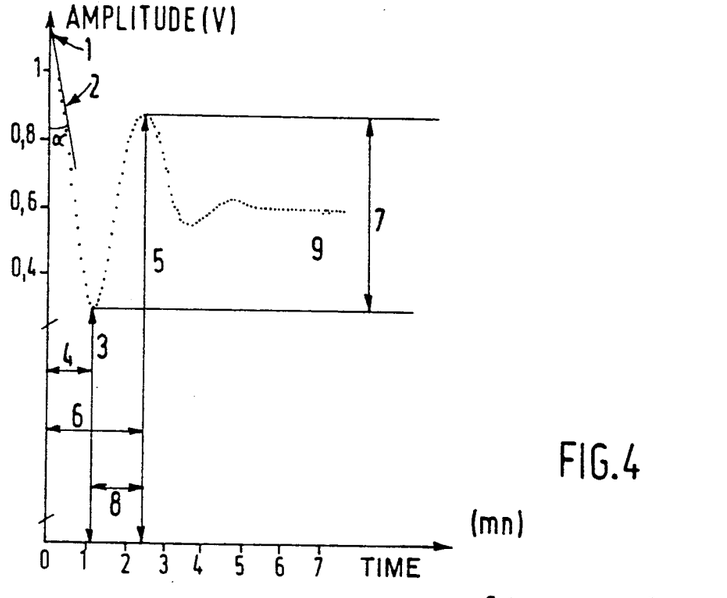
FIG. 4 is a curve showing the variation in amplitude of a signal obtained as a function of the sedimentation time for a suspension of particles according to example 1.

FIG. 4 shows the variation in the signal obtained with the device described above as a function of the sedimentation time for a suspension of particles with a diameter of 15.5 $\mu$m and a density of 1.312. The experimental parameters that can be deduced from this curve are:
1. Initial amplitude, Ao;
2. Initial slope, $\alpha$;
3. Amplitude of the first minimum, Am;
4. Time of occurrence of the first minimum, tm;
5. Amplitude of the first maximum, AM;
6. Time of occurrence of the first maximum, tM;
7. Peak-to-peak amplitude, Acc=AM−Am;
8. Peak-to-peak time, tcc=tM−tm;
9. Final amplitude, Af.

B. Comparison between two types of particles.

TABLE 1

| Diameters | 7 $\mu$m | 15.5 $\mu$m |
|---|---|---|
| Amplitude $A_o$ (mV) | 1062 | 1050 |
| Initial Slope$\alpha$ (mV/mn) | 87 | 714 |
| Amplitude $A_m$ (mV) | 260 | 360 |
| Time $t_M$ (s) | 340 | 63 |
| Amplitude $A_M$ (mV) | 810 | 845 |
| Time $t_M$ (s) | 670 | 135 |
| Amplitude $A_{cc}$ (mV) | 550 | 485 |
| Time $t_{cc}$ (s) | 330 | 72 |
| Amplitude $A_f$ (mV) | 565 | 605 |

Table 1 gives the results obtained on the basis of two types of particle having diameters of 7.0 $\mu$m and 15.5 $\mu$m respectively.

C. Three-dimensional representation of the signal.

Figures 5A, 5B:
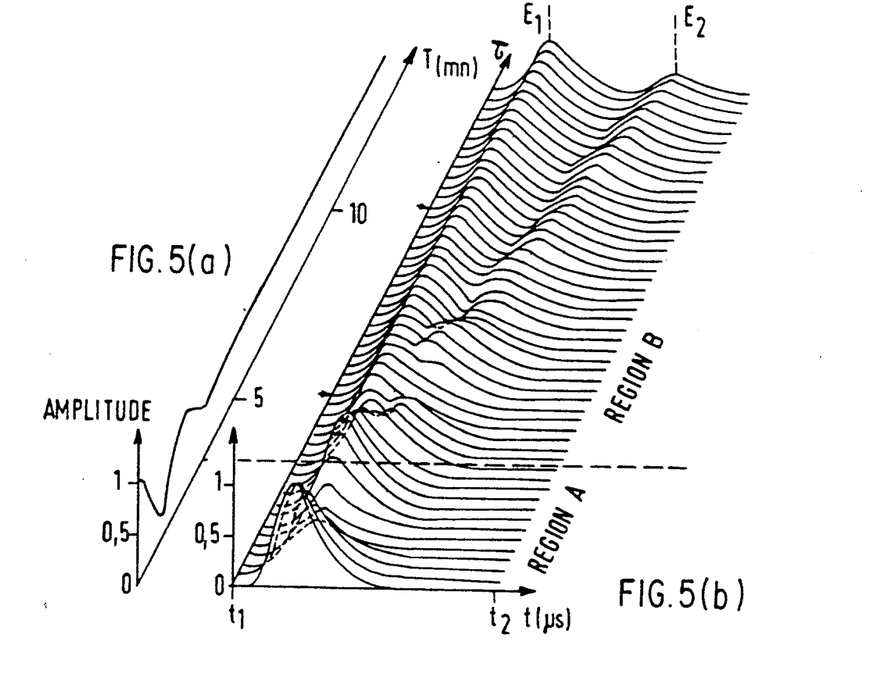
FIGS. 5a-5b are curves, showing in three-dimensional representation, the variations in amplitude of the maximum value of the signal measured as a function of the sedimentation time and of the time taken by the ultrasonic wave to travel the distance between the probe and the interfaces.

FIGS. 5a–5b present the variations of the signal both as a function of the travel time t (time taken by the ultrasonic pulse to cover the to and from distance between the probe and the interfaces) and of the sedimentation time T for a suspension of particles having a diameter of 7.0 $\mu$m at a volume concentration of 5%. The curve represented the progression as a function of the sedimentation time, of the maximum value of the signal measured in the time window t1, t2, represented at b. Two regions, A and B, are perfectly distinguishable. In region A, the oscillations of the signal represent the result of the interferences between the ultrasonic waves reflected respectively by the plate-sediment and sediment-suspension interfaces I1 and I2. Region B shows that echo E2 moves progressively away from echo E1, which means that interface I2 moves progressively away from interface I1.

II—Example of Biological Particles: Suspension of Non-Aggregated Red Blood Cells After normal red blood cells have been washed in a PBS buffer solution, the sediment obtained after centrifuging is resuspended in the same buffer solution at the desired haematocrit.

A. Example of curve obtained.

Figure 6:
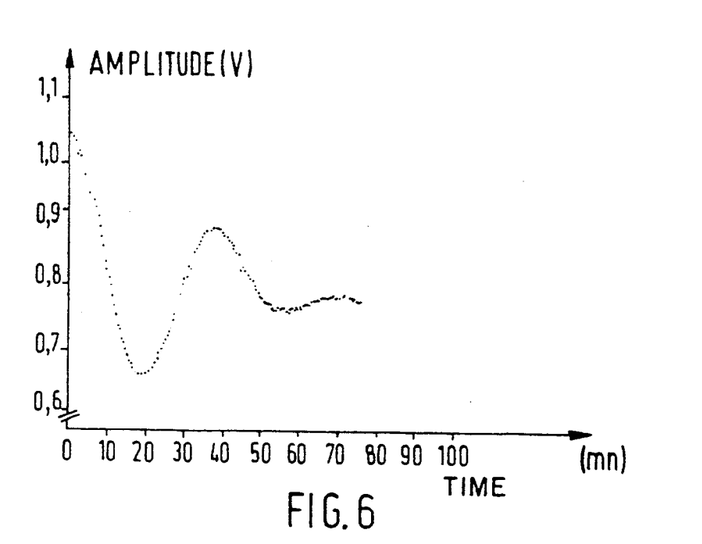
FIG. 6 is a curve analogous to that in FIG. 4 according to example II.

FIG. 6 shows the variation in the signal as a function of the sedimentation time for a suspension of red blood corpuscles at a haematocrit of 2%. The shape of the curve obtained is the same as that already shown for suspensions of particles. The same parameters 1, 2, 3, .. ., 9 can be defined on this curve.

B. Example of results obtained for pathological red blood cells.

Figure 7:
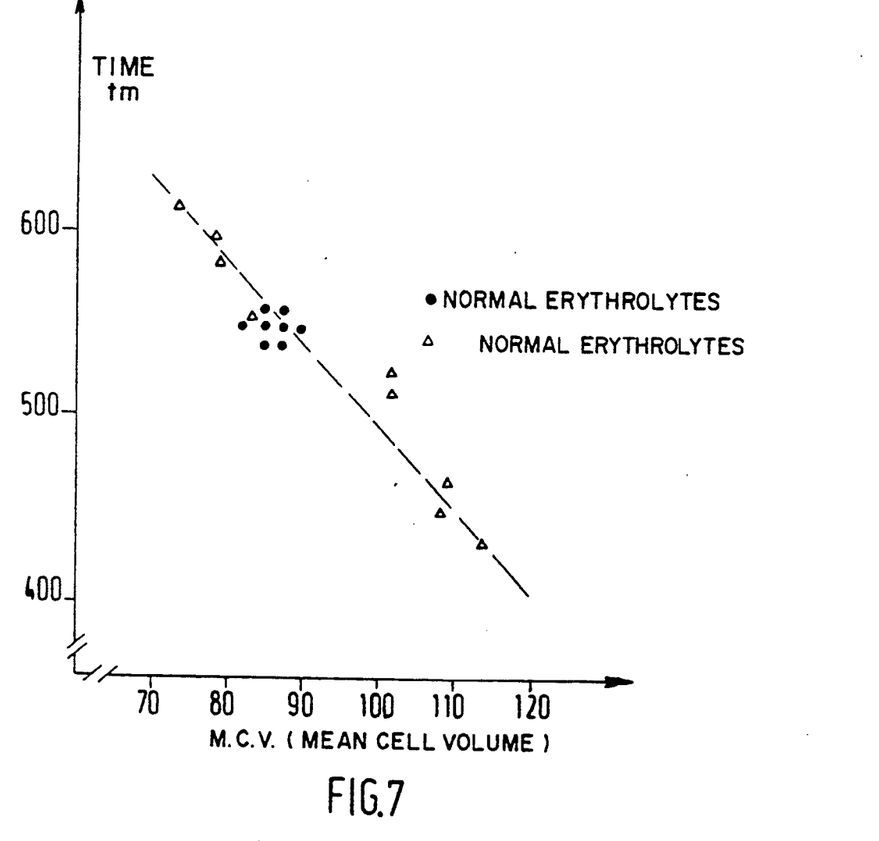
FIG. 7 is a curve of time variation as a function of the mean red cell volume according to example II.

FIG. 7 shows the variation in time of the first minimum tm as a function of the mean red cell volume VGM for normal and pathological red blood cells.

III—Example of Particle Aggregation: Suspensions of Aggregated Red Blood Cells A. Example of curve obtained.

Figure 8:
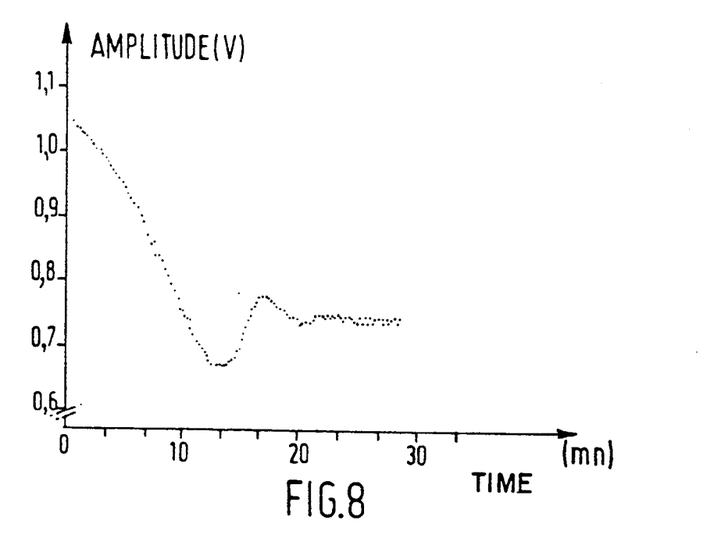
FIGS. 8 to 10 are curves analogous to those in FIG. 4 according to example III.

A suspension of aggregated red blood cells was prepared by resuspending a fraction of the sediment of red blood cells, obtained after centrifuging, in their own plasma at a haematocrit of 2%. FIG. 8 shows the variation in the signal obtained as a function of the sedimentation time.

B. Comparison between results obtained for suspensions of aggregated and non-aggregated red blood cells.

TABLE 2

| Red Blood Cells | aggregated | non aggregate |
|---|---|---|
| Amplitude $A_o$ (mV) | 984 | 1061 |
| Initial Slope$\alpha$ (mV/mn) | 13 | 4 |
| Amplitude $A_m$ (mV) | 696 | 660 |
| Time $t_m$ (s) | 825 | 2280 |
| Amplitude $A_M$ (mV) | 775 | 900 |
| Time $t_M$ (s) | 1065 | 4440 |
| Amplitude $A_{cc}$ (mV) | 79 | 240 |
| Time $t_{cc}$ (s) | 240 | 2160 |
| Amplitude $A_f$ (mV) | 743 | 800 |

Table 2 presents a comparison of the different parameters obtained from a suspension of aggregated red blood cells from a suspension of the same cells non-aggregated.

C. Example of pathological red blood cells.

Figure 9:
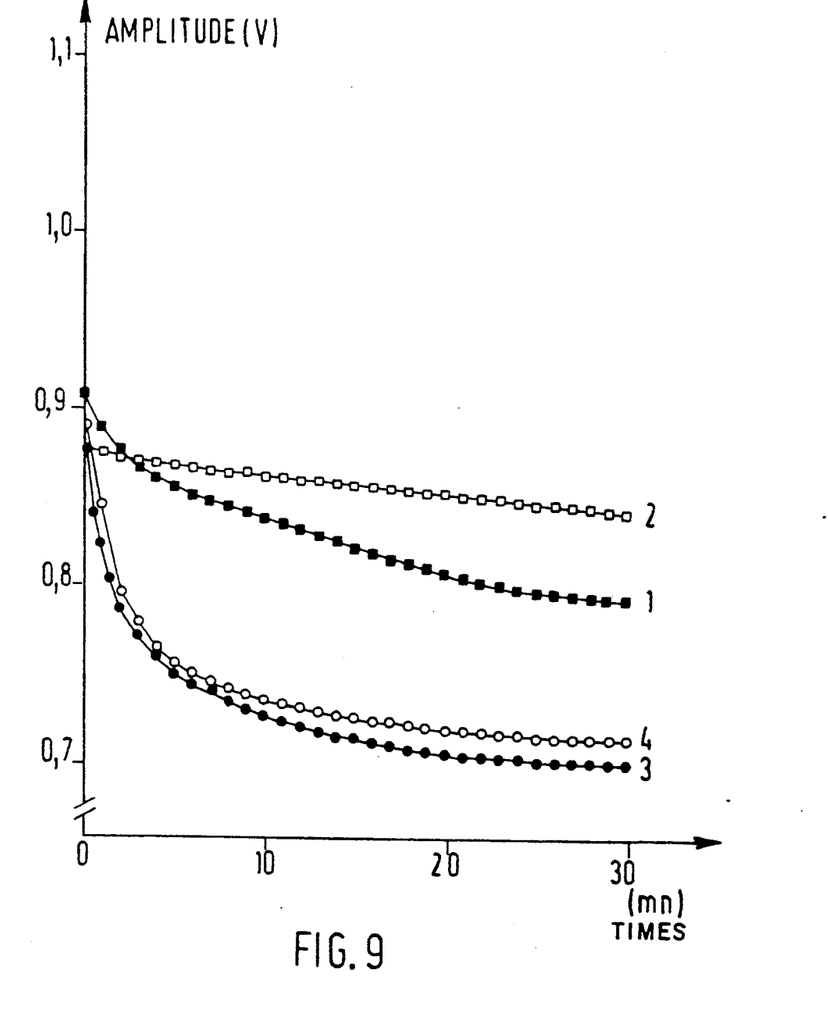

FIG. 9 shows the variations in the signal as a function of the sedimentation time for a suspension of sickle red blood cells at a haematocrit of 25% for different partial pressures in oxygen. Curve 1 was obtained directly on veinous abnormal blood of a patient having sickle cell anemia whose partial pressure in oxygen (pO2) is 40 mm Hg. Curve 2 was obtained for the same blood, but oxygenated (pO2$\simeq$150 mm Hg). Curve 3 was obtained for the same blood but de-oxygenated (pO2$\simeq$0 mm Hg). Curve 4, obtained for normal blood (oxygenated or de-oxygenated) is presented for the purposes of comparison. It is perfectly clear from this figure that sickle cells behave in a very particular manner according to the pO2.

D. Example of aggregation of red blood cells in the presence of normal or pathological plasma.

Figure 10:
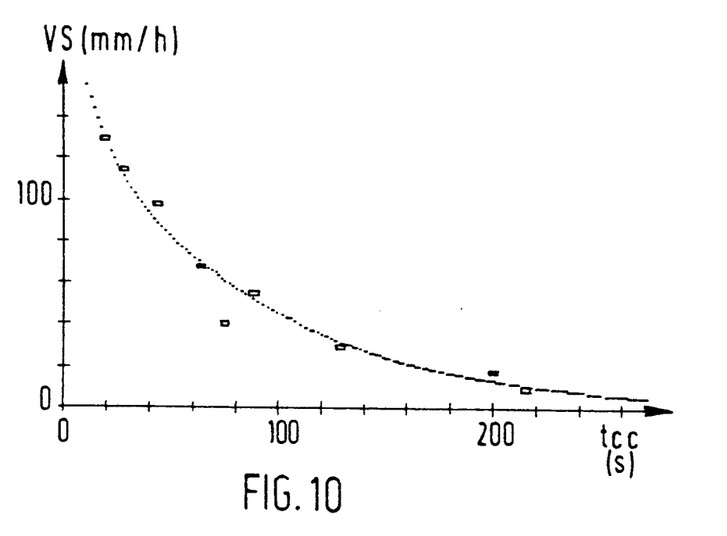

Suspensions of red blood cells were prepared at a haematrocrit of 8% by mixing the cells in 36% of plasma, normal or pathological, and 56% of PBS buffer solution. FIG. 10 shows the variations in time Tcc as a function of the sedimentation rate measured using the Westergren method. The difference in behaviour between these two kinds of blood derives from the abnormal presence of proteins in abnormal quantities in the pathological blood.

E. Example of agglutination of red blood corpuscles.

Figure 11:
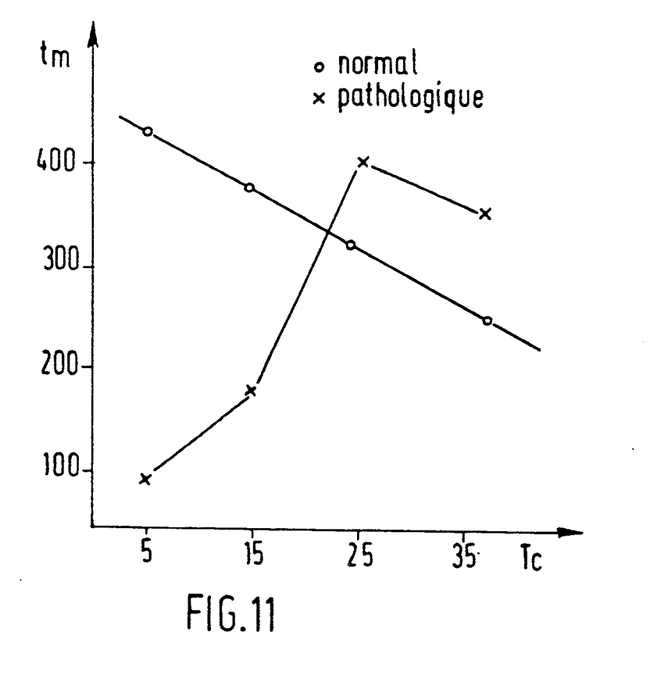
FIG. 11 is a curve showing the aggregation of the red blood cells as a function of temperature.

The blood-bank methods of analysis of blood groups and the immuno-haematological methods are based on studies of the agglutination of red blood corpuscles by antibodies. An example of agglutination by a pathological cold agglutinin is compared with the aggregation of red blood cells for normal blood in FIG. 11 in which tm is represented as a function of the temperature.

We claim:

1. A device for detecting and analyzing a suspension of particles settling in a fluid based upon interference of ultrasonic waves, said device comprising:

a thermostatically controlled measuring cell in the form of a hollow vertical cylinder, said hollow vertical cylinder is traversed by a thin plate which is positioned perpendicular to a vertical axis of the hollow vertical cylinder, said thin plate splitting said hollow vertical cylinder into two cavities, one of the two cavities to receive the suspension of particles, said hollow vertical cylinder is integrated in a thermostatically controlled enclosure surrounding vertical side portions of said hollow vertical cylinder;

a transmitting-receiving ultrasonic probe connected to said measuring cell and located in the other of the two cavities at a distance from the thin plate;

an echograph, connected to said ultrasonic probe, generating electric pulses having a variable repetition period which excite the ultrasonic probe, said echograph detecting and converting said electric pulses into electric signals;

a signal acquisition means, connected to said echograph, for acquiring said electric signals, said signal acquisition means including, a delay means for introducing a variable delay in relation to transmission by the ultrasonic probe, a sample and hold means for sampling and holding the electric signals stroboscopically in a given time slot, and an analog-digital converter; and a means for digitally reconstructing an echo from the given time slot and for supplying a screen with representative curves of the echo.

2. Device according to claim 1, wherein the ultrasonic probe is positioned in the other of the two cavities by a tight plug which closes said other of the two cavities, said tight plug is provided with a small closable conduit, and a volume of fluid fills the other of the two cavities, between the plate and the probe.

3. Device according to claim 1, wherein the ultrasonic probe is a material capable of emitting ultrasounds having an operating frequency determined as a function of a measurement to be made.

4. Device according to claim 1, wherein the echograph is constituted by an amplifier formed by an integrated circuit, and least one of a rectifier and an analog filter for frequency analysis.

5. Device according to claim 1, wherein the variable delay allows the electric signal to be sampled in the given time slot.

6. Device according to claim 5, wherein an amplitude of the electric signal is digitized by the analog-digital converter and stored in a micro-computer, all of the electric signals belonging to the time slot being stored to digitally reconstruct the analog signal reflected by the interface plate/suspension.

7. Device according to claims 1 or 5, wherein the time slot is positioned on an echo generated by an interface between the thin plate and the suspension of particles before the sample and hold means samples the electric signal contained in the time slot by the variable delay.

8. Device according to claims 1 or 5, wherein the sample and hold means effects, on the basis of a pulse emitted, a succession of acquisitions of the reflected signal at an interface plate/suspension starting from a first time, each acquisition being incremented by a step delay in relation to a preceding acquisition.

* * * * *